United States Patent [19]
Shimoda

[11] Patent Number: 5,906,638
[45] Date of Patent: May 25, 1999

[54] ELECTROTHERAPY DEVICE, BAND WITH SKIN ADHERING CHARGE CARRYING PADS, AND CHARGING DEVICE

[76] Inventor: Setsuo Shimoda, 100, Ooaza Hario, Asahi-mura, Higashitikumagun, Nagano-ken, Japan

[21] Appl. No.: 08/988,374

[22] Filed: Dec. 10, 1997

[30] Foreign Application Priority Data

Dec. 16, 1996 [JP] Japan ..................... 8-335331
Jul. 31, 1997 [JP] Japan ..................... 9-205602

[51] Int. Cl.$^6$ ..................... A61F 13/00
[52] U.S. Cl. ..................... 607/152; 607/1
[58] Field of Search ..................... 607/1, 2, 152; 600/372, 382

[56] References Cited

U.S. PATENT DOCUMENTS

| | | |
|---|---|---|
| 4,817,594 | 4/1989 | Juhasz ..................... 607/152 |
| 5,218,973 | 6/1993 | Weaver et al. ..................... 607/152 |
| 5,397,338 | 3/1995 | Grey et al. . |
| 5,514,165 | 5/1996 | Malaugh et al. . |

*Primary Examiner*—Scott M. Getzow
*Attorney, Agent, or Firm*—Armstrong, Westerman, Hattori, McLeland & Naughton

[57] ABSTRACT

To provide a user friendly electrotherapy device not large in space taken and not requiring a human operator or special treatment time, the electrotherapy device uses as a skin adhering charge carrying pad a soft kneaded material comprising a silicone rubber as a binder in which a fine powder of mugwort charcoal etc. is mixed and kneaded well. The ratio of mixture of the powder of charcoal with respect to the silicone rubber is preferably at least 5 wt %. This skin adhering charge carrying pad is superior in the sustainability of the charge. Many reports of good results have been obtained by just continuously adhering pads to suitable locations of the body in accordance with the symptoms.

16 Claims, 7 Drawing Sheets

ELECTROTHERAPY DEVICE, BAND WITH SKIN ADHERING CHARGE CARRYING PADS, AND CHARGING DEVICE

BACKGROUND OF THE INVENTION

1. Field of the Invention

The present invention relates to an electrotherapy device suited for providing therapy adhered to the skin.

2. Description of the Related Art

In the past, there has been known an electrotherapy device applying a weak current of a high potential to a seated body and repeating this over several days so as to treat arthritis, backaches, aching shoulders, languidity, fatigue, chills, poor blood circulation, and other chronic symptoms of unknown cause. There is little scientific or theoretical explanation of why application of an alternating current of a high potential (several thousand volts) "cures".

Everyone suffers from one of the chronic symptoms characteristic of middle and old age where this type of chronic pain or hardship persists. This being said, the extent of suffering of a person is not something judged objectively, but can only be understood by the statements of the person in question, so frequently tends to be ignored. Further, if the person in question pays too much attention to it, the reliability of his or her statements becomes questionable and conversely delays the determination of the cause. Accordingly, for this type of symptom, the general treatment is first applied and the result then examined. As such treatment, there are electrotherapy, magnetotherapy, heat and hot spring therapy, "shiatsu" finger-pressure therapy, acupuncture and moxibustion, vibration therapy, and other physical therapy.

It is well known that the voltage and potential of the body fluids play an important role in the tissue, organs, cellular level, and nervous system of the human body. Electrical factors are highly involved in ensuring the autonomous homeostasis of the body.

The afore-mentioned electrotherapy, however, applies too unnaturally high a potential (several thousand volts) from the outside to substantially the entire body in an unlimited manner and therefore is nothing more than a kind of electric shock treatment. Repeated exposure to a high potential over several days, while painless to the person in question, must be said to rather be an extreme measure and may do much more harm than good.

From this standpoint, the present inventor engaged in intensive studies to find a new type of electrotherapy and as a result found that it is necessary to limit the area treated (diseased area or pressure point) such as seen in shiatsu therapy and acupuncture and moxibustion and that it is suitable to give some sort of electrical stimulus to such an area treated. The problem is to "give . . . electrical stimulus". For example, giving voltage or a current to the area treated, while the therapeutic significance is unknown, resembles local electric shock acting forcibly from the outside.

In view of this problem, the present inventor found that even patients complaining about such chronic symptoms of unknown cause can be said to be merely suffering from a slight collapse of their autonomic balance and arrived at the idea that it was sufficient to induce an autonomic recovery from this unbalance (unclear point). Accordingly, what should be done to the body from the outside is to "sustain" the procedure of "guiding" the treated area.

SUMMARY OF THE INVENTION

Therefore, a new electrotherapy device realizing such sustained electrical guidance on a local area must meet the following requirements.

That is, the first object of the present invention is to provide a user friendly electrotherapy device not large in space taken and not requiring a human operator or special treatment time.

A second object of the present invention is to provide an electrotherapy device able to reduce the cost of treatment.

To attain the above objects, the present inventor arrived at the idea of using a skin adhering charge carrying pad as the new electrotherapy device. If this skin adhering charge carrying pad is directly or indirectly adhered to the treated area, the charge caused by the electrostatic induction is concentrated locally at the ski where the pad is adhered, so the electrostatic field penetrates deep through the skin directly underneath it. So long as the skin adhering charge carrying pad is adhered to the treated area, the above local electrostatic field will continue penetrating into the body. The amount of the charge of the skin adhering charge carrying pad, however, gradually decreases due to discharge into the air etc., so it is necessary to select one with a high sustainability of the charge in order to realize a practical skin adhering charge carrying pad.

Therefore, the present inventor studied various charge carrying substances and as a result discovered that it was best to use a soft material or elastic material comprised of a plastic insulating substance in which a powder of charcoal is dispersed as the skin adhering charge carrying pad. If a powder of charcoal of a conductor is dispersed in a plastic insulating substance, electrostatic electrons (e−) collect around the carbon (C) atoms and give a negative charge as a whole as for example in an ebonite rod. With a rigid body (hard substance) such as an ebonite rod, when adhered closely to the skin using a tape etc., there is a strong discomfort upon contact with the skin and therefore, from the viewpoint of sustainability, long term adhesion is impossible.

Due to this situation, the present inventor succeeded in eliminating the discomfort at the time of adhesion to the skin by using a soft kneaded material such as a soft material or elastic material comprised of a plastic insulating substance as a binder for the skin adhering charge carrying pad. In particular, if a plastic insulating substance such as a silicone rubber is used as the binder, the viscoelasticity and kneadability an be maintained as they are. Rekneading is possible at any time by the fingers etc. The friction from the kneading generates an abundant amount of static electricity. The electrons accumulate around the carbon atoms to generate a high charge, so regeneration of the charge carrying pad becomes easy and repeated use becomes possible.

Further, as the powder of charcoal, it is possible to use carbon black or other mineral charcoal. Experiments, however, show that when carbon black powder is dispersed in the kneading material, the amount of charge carried ends up halving in about one day just be standing in an air environment and therefore the sustainability of the charge is short.

Therefore, the present inventor studied the sustainability of the charge using various types of charcoal and discovered that the sustainability of the charge is longer if plant charcoal is used rather than mineral charcoal. The reason is unknown, but the sustainability of the charge becomes stronger when an inorganic element other than carbon is included as an impurity rather than carbon black of a high purity of carbon. Among these, mugwort charcoal has a high charge carrying property and high sustainability.

Further, the present inventor investigates the ratio of mixture of the powder of charcoal when using a silicone rubber as a binder, whereupon he discovered that the charge carrying property is saturated at about 5 wt %. In the case of mugwort charcoal, the charge carrying property is highest.

Therefore, it is preferable to mix at least 5 wt % charcoal powder. Mixture of an extreme amount over 30% probably will lead to deterioration of the charge carrying property since the conductivity is increased.

The inventor conducted clinical experiments adhering a skin adhering charge carrying pad comprised of this soft kneaded material such a soft material or elastic material as an electrotherapy device to a diseased area or pressure point, whereupon numerous reports were received of good effects on various symptoms.

The above skin adhering charge carrying pad is adhered to the skin using a sticking plaster etc., but it is also possible to use a band with skin adhering charge carrying pads which is able to be attached without using a sticking plaster. This band with skin adhering charge carrying pads is comprised of an attachment band to which one or more of the skin adhering charge carrying pads are attached to at least one side, conductive wiring connected to the skin adhering charge carrying pads along said attachment band, and power terminals provided at part of the conductive wiring. By attaching this band to the body, it is possible to apply an electrostatic field to a plurality of diseased areas or pressure points and improve the ease of use. Further, if a charge is applied to the power terminals, it is possible to replenish the charges carried by the charge carrying pads through the conductive wiring and achieve sustainability of the electrostatic field.

Further, by using a charging device for replenishing the carried charge to the skin adhering charge carrying pads, it is possible to achieve the easy replenishment of the charge to charge carrying pads which have weakened in charge.

BRIEF DESCRIPTION OF THE DRAWINGS

The above objects and features as well as other features of the present invention will be more apparent from the following description of the preferred embodiments with reference to the accompanying drawings, wherein.

DESCRIPTION OF THE PREFERRED EMBODIMENTS

Next, examples of the present invention will be explained based on the attached drawings.

EXAMPLE 1

Figure 1:
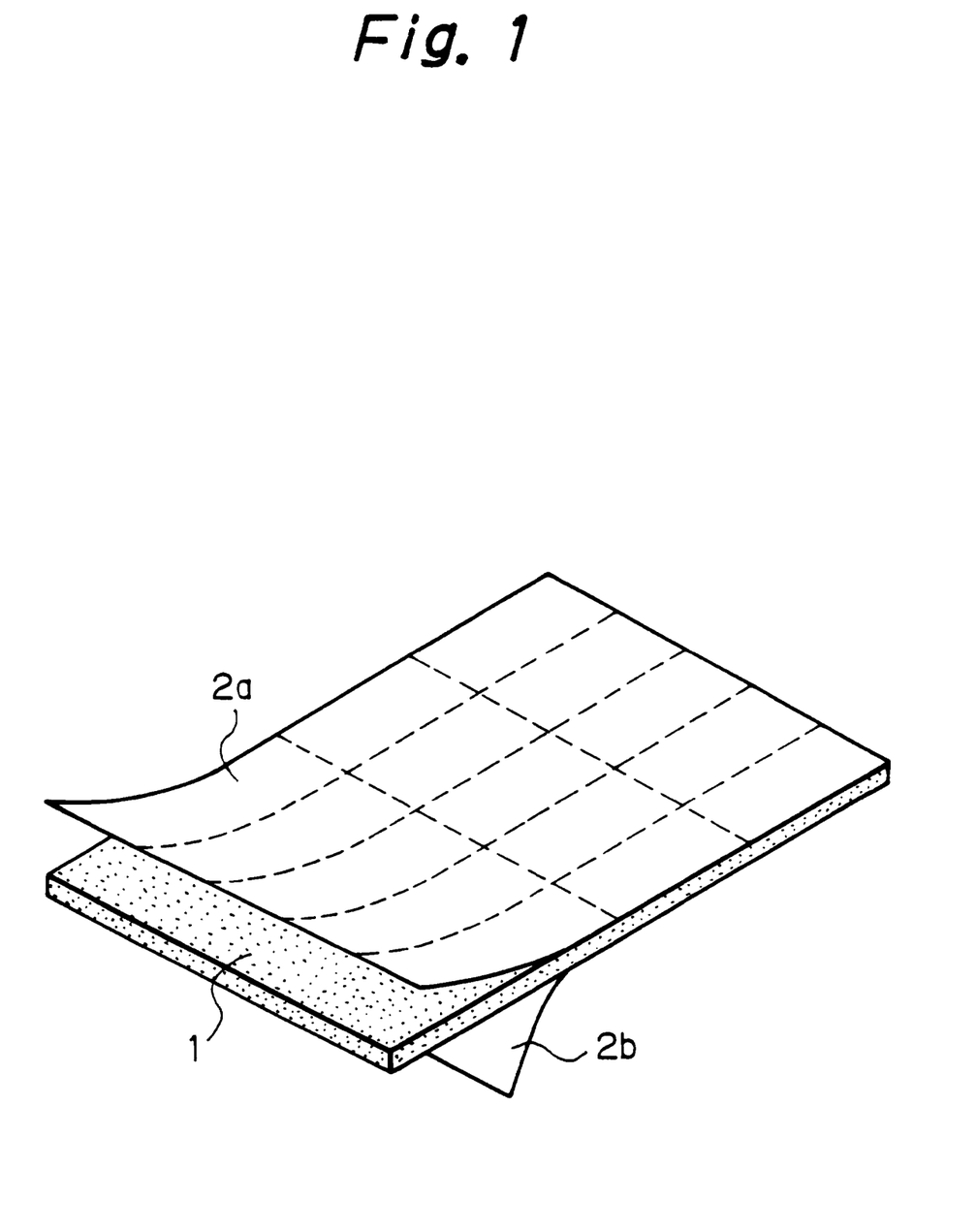
FIG. 1 is a perspective view of a skin adhering charge carrying pad as an electrotherapy device according to an embodiment of the present invention.

FIG. 1 is a perspective view of a skin adhering charge carrying pad of an electrotherapy device according to Example 1 of the present invention. This skin adhering charge carrying pad is obtained by using a silicone rubber (plastic insulating substance) as a binder, mixing a fine powder of charcoal into this, and mixing well to disperse the powder in it. For sale, it is shaped into the sheet like kneaded material 1 shown in FIG. 1 which is used by treating it into suitable sizes. In the middle of the kneading, the static electricity generated by the friction of the kneading is discharged. The front and reverse of the sheet like kneading material 1 shaped into a thin sheet are covered by insulating films 2a and 2b with perforations for division. Note that it is also possible to use latex or another vulcanized rubber as the binder.

The type of the power of charcoal mixed together with the silicone rubber (RTVKE45 made by Shinetsu Kagaku Kogyo Inc.) is selected from carbon black, oak charcoal, bamboo charcoal, and mugwort charcoal. Consideration is given to the relationship between the time elapsed from a reference point of 10 hours after the end of the kneading and the potential difference due to the charging. The time 10 hours after the end of the kneading is used as a reference point because the charge carried is too strong directly after kneading and measurement ends up becoming impossible or unstable. For the measurement, use is made of a millivolt potential difference meter, that is, a D-13 type measurer made by Horiba Seisakusho (Glass Electrode ORP Meter).

Figure 2:
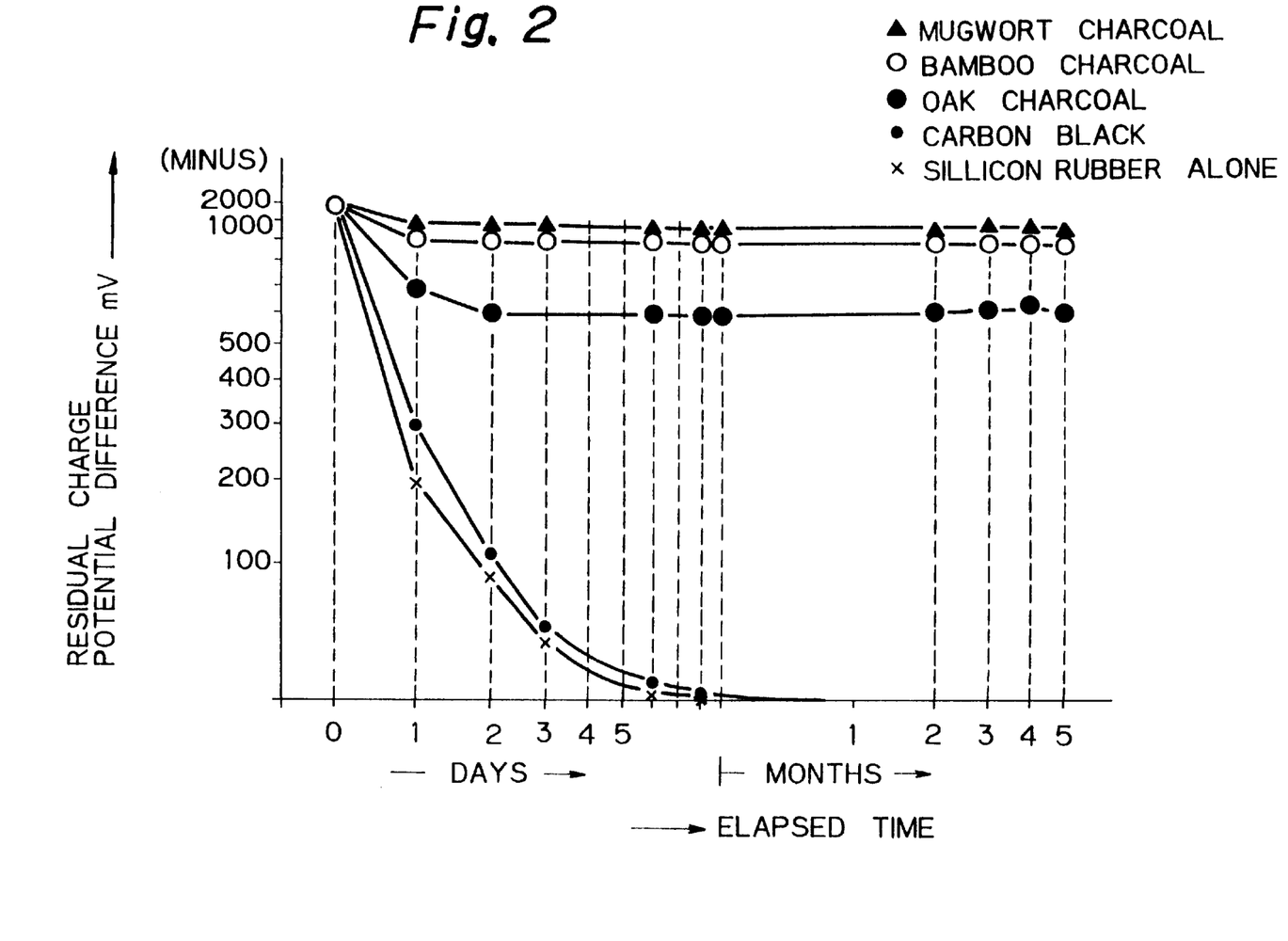
FIG. 2 is a graph of the time dependency of the residual charging potential difference for a kneaded material obtained by kneading silicone rubber and powder of various charcoals.
Figure 3:
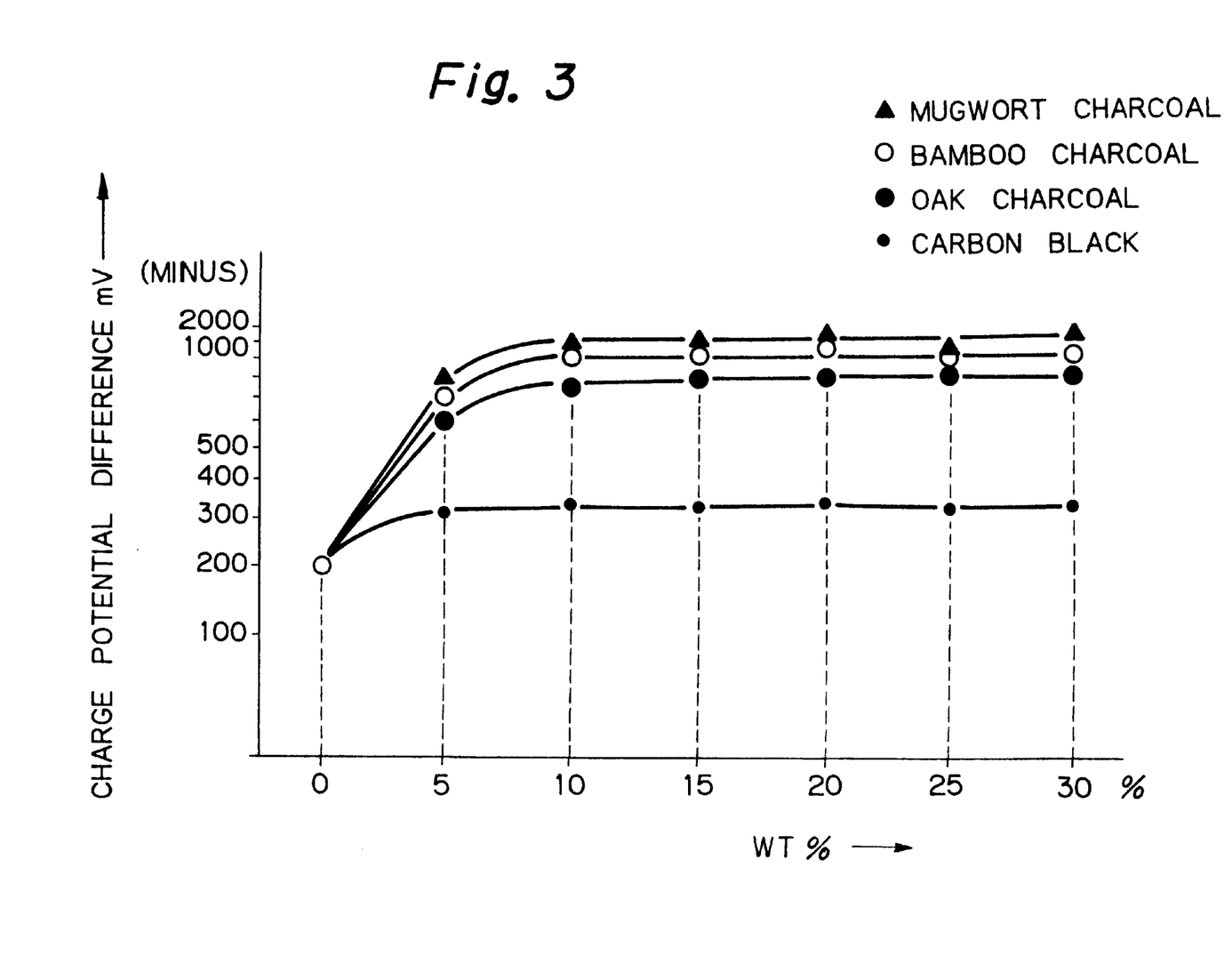
FIG. 3 is a graph of the dependency of the charging potential difference on the ratio by weight of the charcoal powder for a kneaded material obtained by kneading silicone rubber and powder of various charcoals.

As shown in the graph of FIG. 2, the residual charge potential difference (mV) of carbon black follows substantially the same trend as the case of just silicone rubber (RTVKE45) and ends up attenuating down to $\frac{1}{10}$ after the elapse of one day. With oak charcoal, bamboo charcoal, and mugwort charcoal, however, there is no sudden attenuation and a gradual attenuation is followed so a sustainability of charge of several months is observed. In particular, with mugwort charcoal, the rate of attenuation is extremely low. It is learned that it has the greatest sustainability of charge among all plant charcoal.

Further, consideration was given to the dependency of the charge carried on the charcoal powder content. FIG. 2 shows the charge potential difference at the point of time 10 hours after the end of kneading with respect to the percent weight of fine powder charcoal mixed into the silicone rubber (RTVKE45 made by Shinetsu Kagaku Kogyo Inc.). In the case of all of the charcoal powder, it was learned that the charge carrying property was saturated at about 5 wt %. Among these, the charge carrying property was highest in the case of mugwort charcoal. Therefore, as the skin adhering charge carrying pad, it is desirable to mix in 5 wt % of charcoal powder. In this experiment, the amount mixed in was stopped at 30 wt %. If the ratio is increased, probably the charge carrying property will conversely deteriorate since the conductivity is increased.

Figure 4:
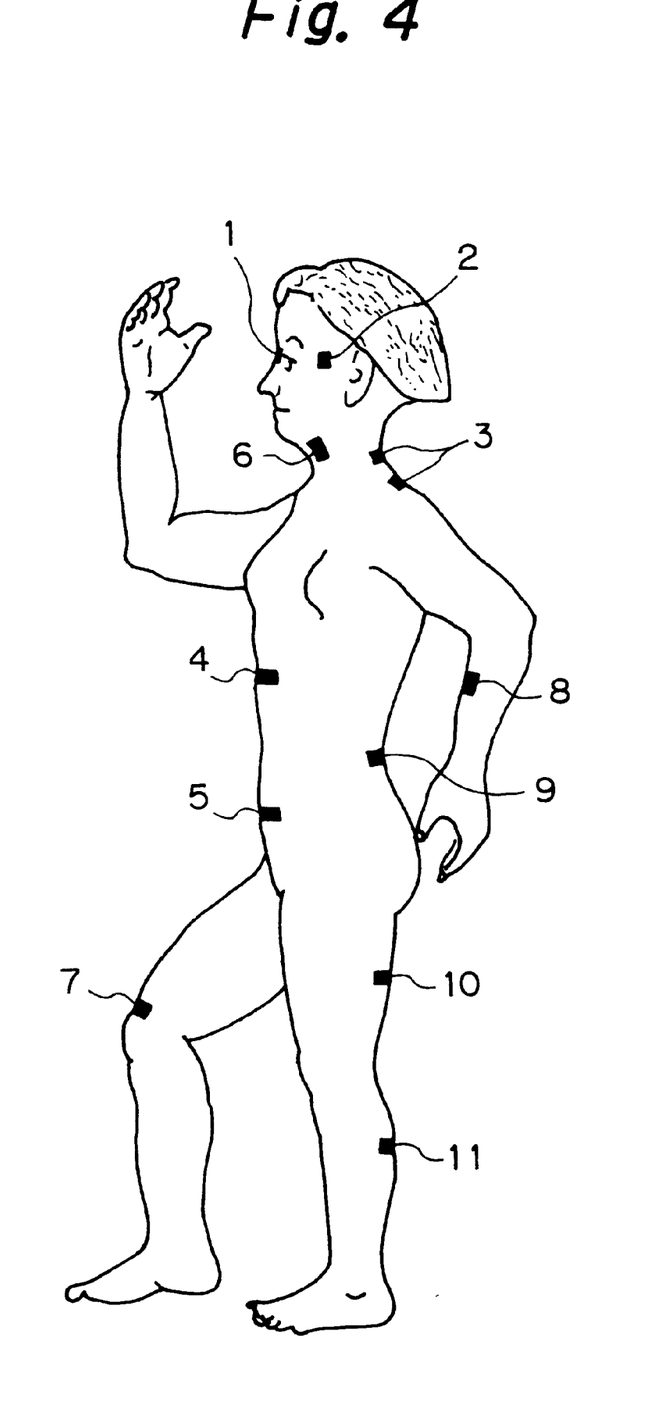
FIG. 4 is an explanatory view of the state where a sheet like kneading material using mugwort charcoal is suitably adjusted in size to the symptoms and adhered to various positions of the body.

The sheet like kneading material 1 using mugwort charcoal is torn into a suitable size and adhered by sticky plaster etc. to the treated area (diseased areas or pressure point) shown in FIG. 4 in accordance with the symptoms. It may be directly brought into contact with the skin as well. Further, it may be adhered through gauze, nonwoven fabric, paper, etc. It may be affixed using adhesive tape etc. When clinical experiments were performed, many reports were obtained of good effects regarding various symptoms. Examples of the reports are given below.

TABLE 1

(Runny Nose)

| Patient | Symptoms | Adhered position | Results |
|---|---|---|---|
| A1 | Runny nose due to cold | 1 | Stopped immediately |
| A2 | Suffered from constant runny nose | 1 | Stopped immediately (started again after removal) |
| A3 | Suffered from runny nose during trip | 1 | Stopped immediately |
| A4 | Runny nose due to cold | 1 | Stopped immediately |
| A5 | Runny nose | 1 | Stopped when adhered, but appeared when removed |

TABLE 2

(Coughs)

| Patient | Symptoms | Adhered position | Results |
|---|---|---|---|
| B1 | Suffered from cough due to cold | 6 | Stopped when adhered |
| B2 | Suffered from night time coughing, and insufficient sleep due to cold | 6 | No more coughing |
| B3 | Suffered from night time coughing due to cold | 6 | Coughing stopped. Started again when removed in morning |
| B4 | Coughing when talking | 6 | No more coughing even if talking |
| B5 | Suffered from coughing when talking on phone | 6 | No more coughing, phone calls possible |

TABLE 3

(Sore Throat)

| Patient | Symptoms | Adhered position | Results |
|---|---|---|---|
| C1 | Coughing and sore throat due to cold | 6 | Sore throat relieved slightly earlier |
| C2 | Coughing and sore throat due to cold | 6 | Sore throat relieved slightly earlier |
| C3 | Coughing and sore throat due to cold | 6 | Sore throat appeared to be relieved slightly earlier |
| C4 | Coughing and sore throat due to cold | 6 | Coughing relieved earlier. Sore throat when relieved |

TABLE 4

(Aching Shoulders)

| Patient | Symptoms | Adhered position | Results |
|---|---|---|---|
| D1 | Aching shoulders due to simple fatigue | 3 | Appears to have worked. Eased when reattached |
| D2 | Aching shoulders due to simple fatigue | 3 | No more need for shoulder massage |
| D3 | Aching shoulders due to simple fatigue | 3 | Eased, so adhered continuously every day |
| D4 | Aching shoulders due to simple fatigue, physically well fleshed | 3 | Became easier in about three hours after being widely adhered |
| D5 | Aching shoulders due to simple fatigue, physically well fleshed | 3 | Became easier |
| D6 | Aching shoulders due to office work | 3 and 8 | Shoulders became lighter in about 40 minutes |
| D7 | Aching shoulders due to office work | 3 and 8 | Aching shoulders became no longer noticeable |
| D8 | Aching shoulders due to simple fatigue | 3 | Adhered for about one hour, then ache no longer noticeable |
| D9 | Baker | 3 | Worked on one shoulder. Became better when reattached |

TABLE 5

(Headache)

| Patient | Symptoms | Adhered position | Results |
|---|---|---|---|
| E1 | Could not sleep due to headache | 2 | Appears to have worked in about 30 minutes. Learned when waking up in morning |
| E2 | Took pain reliever every day | 2 | Relief obtained in 20 to 30 minutes |
| E3 | Took pain reliever every day | 2 and 3 | Believed to have come from shoulders. When attached to 3 in addition to 2, ache relieved in about 30 minutes |
| E4 | Head suddenly began aching | 2 | Immediately cured |

TABLE 6

(Knee Pain)

| Patient | Symptoms | Adhered position | Results |
|---|---|---|---|
| F1 | Pain starting five years ago | 7 | Pain relieved over night |
| F2 | Pain in right knee | 7 | Pain immediately relieved |
| F3 | Pain in left knee and could not sleep at night | 7 | Pain relieved |

TABLE 6-continued (Knee Pain)

| Patient | Symptoms | Adhered position | Results |
| --- | --- | --- | --- |
| F4 | Pain in both knees, hospitalization | 7 | Pain relieved in one day |
| F5 | Pain in right knee | 7 | Pain relieved in one day |
| F6 | Over weight, knee pain when working | 7 | Pain relieved in about two days, work possible |
| F7 | Both knees injured in accident five years ago | 7 | Pain disappeared when waking up, could sit cross-legged |
| F8 | Ankles painful for long period | 10 and 11 | No fatigue next day, work possible |

TABLE 7

(Backache)

| Patient | Symptoms | Adhered position | Results |
| --- | --- | --- | --- |
| G1 | Hospitalization for hernia seven years ago, backache, numbing of left leg | 9 | Backache relieved, numbing weakened |

TABLE 8

(Others)

| Patient | Symptoms | Adhered position | Results |
| --- | --- | --- | --- |
| H1 | Upset stomach and vomiting feeling after meals | 4 | Symptoms relieved after about 20 minutes |
| H2 | Acute stomach ache | 5 | Returned to normal after about 30 minutes and able to eat. |
| H3 | Suffered from ear ache | Ear lobe | Complete relieved in 30 minutes. |
| H4 | Constipated and ingested medicine daily | 5 | Medicine became unnecessary and bowel movement became daily |
| H5 | Diarrhea conditions continued | 5 | Diarrhea conditions disappeared |
| H6 | Constipation | 5 | No change |

EXAMPLE 2

Figure 5A:
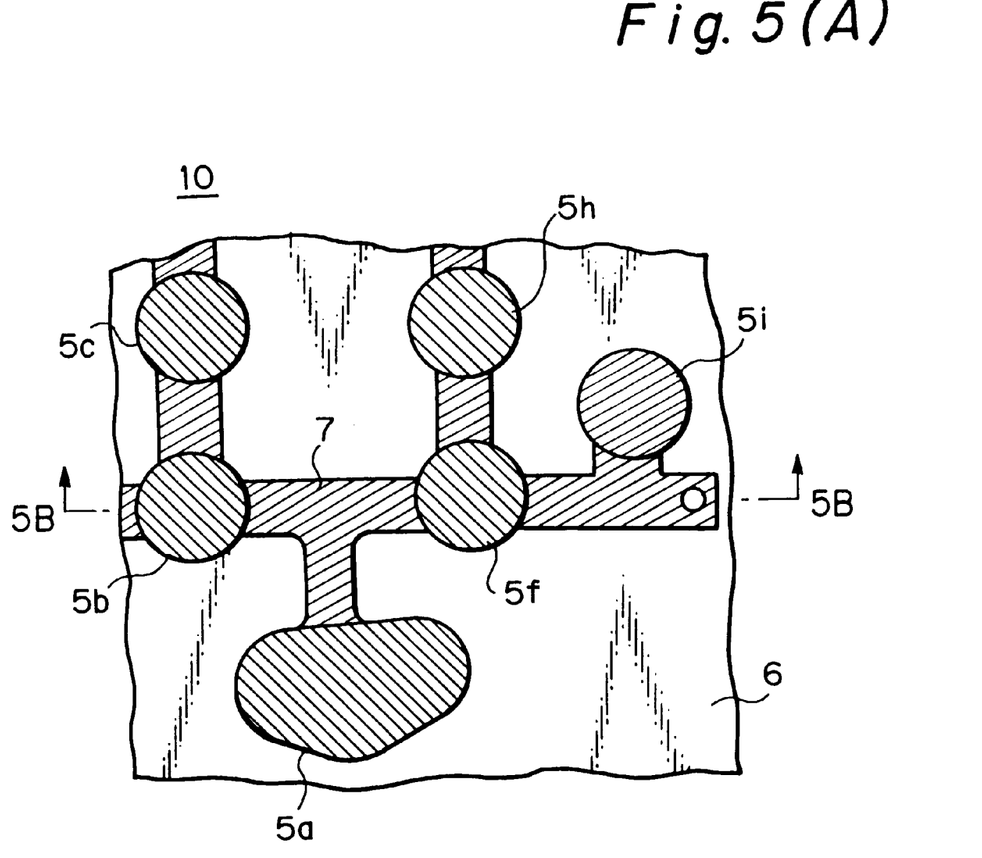
FIG. 5(A) is a partial plane view of a band with skin adhering charge carrying pads according to Example 2 of the present invention.
Figure 5B:
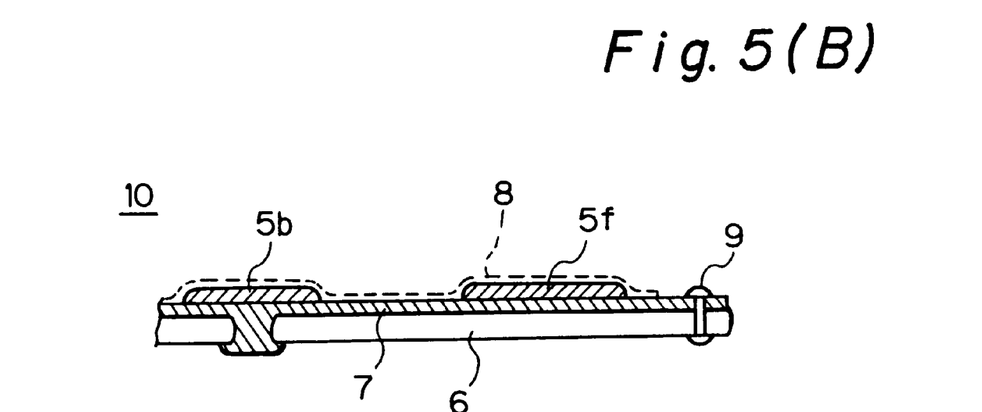
FIG. 5(B) is a cut perspective view of the state cut away along the line B—B in FIG. 5(A)
Figure 6:
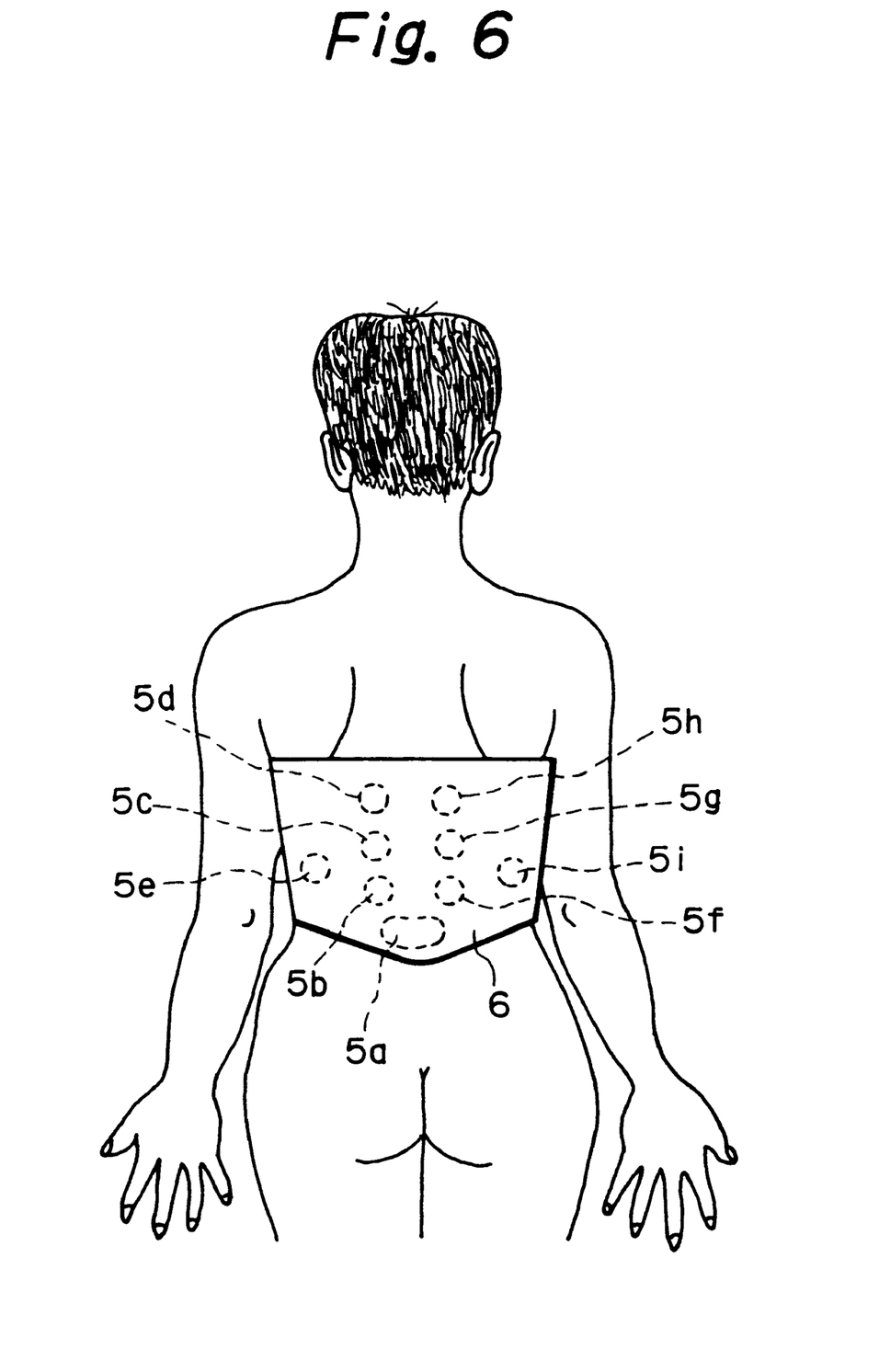
FIG. 6 is a back view of a person wearing the band with the skin adhering charge carrying pads.

FIG. 5(A) is a partial plane view of a band with skin adhering charge carrying pads according to Example 2 of the present invention, FIG. 5(B) is a cutaway view showing the state cut along the line B—B in FIG. 5(A), and FIG. 6 is a back view of the human body with a band with skin adhering charge carrying pads attached.

The band 10 with skin adhering charge carrying pads of this example uses substantially round skin adhering charge carrying pads 5 (5a to 5i) obtained by dividing the sheet like kneading material 1 according to Example 1 into suitable sizes. That is, the band 10 with skin adhering charge carrying pads it comprised of a flexible attachment band 6 able to be wrapped around the waist, a thin layer like conductive wiring 7 laid around one side (reverse side) of the attachment band 6, skin adhering charge carrying pads 5a to 5i attached at separate locations at predetermined portions of the conductive wiring 7, and a protective fabric 8 covering the charge carrying pads 5a to 5i and the conductive wiring 7. The charge carrying pads 5a to 5i are arranged at locations corresponding to the pressure points of the waist. The conductive wiring 7 is power wiring for replenishing the charge of the charge carrying pads 5a to 5i. Rivet shaped power terminals 9 are provided at parts of the same.

Such a band 10 with skin adhering charge carrying pads is wrapped around the waist so that the charge carrying pads 5a to 5i correspond to the pressure points of the waist. The charge carrying pads 5a to 5i carry a charge, so the charge due to the electrostatic induction collects locally at the skin of the adhered portions, so the electrostatic field penetrates deep below the skin directly beneath the same. When the attachment time becomes longer, the charge carrying pads 5a to 5i lose the charge and the electrostatic field gradually weakens. In such a case, the electrostatic field can be sustained by bringing a negative electrode of a charging device into contact with the power terminal 9 and injecting a negative charge to replenish the charge of the charge carrying pads 5a to 5i.

The charging device, when a commercial power supply is used, may be comprised of a rectifier diode circuit (for example, a diode bridge circuit) and a smoothing capacitor. A battery and capacitor are also acceptable. The charge carrying pad 5 and the skin where it is adhered constitute a type of capacitor, so it may also be constituted by a piezoelectric element and rectifier diode rectifying the pulse current.

Figure 7A:
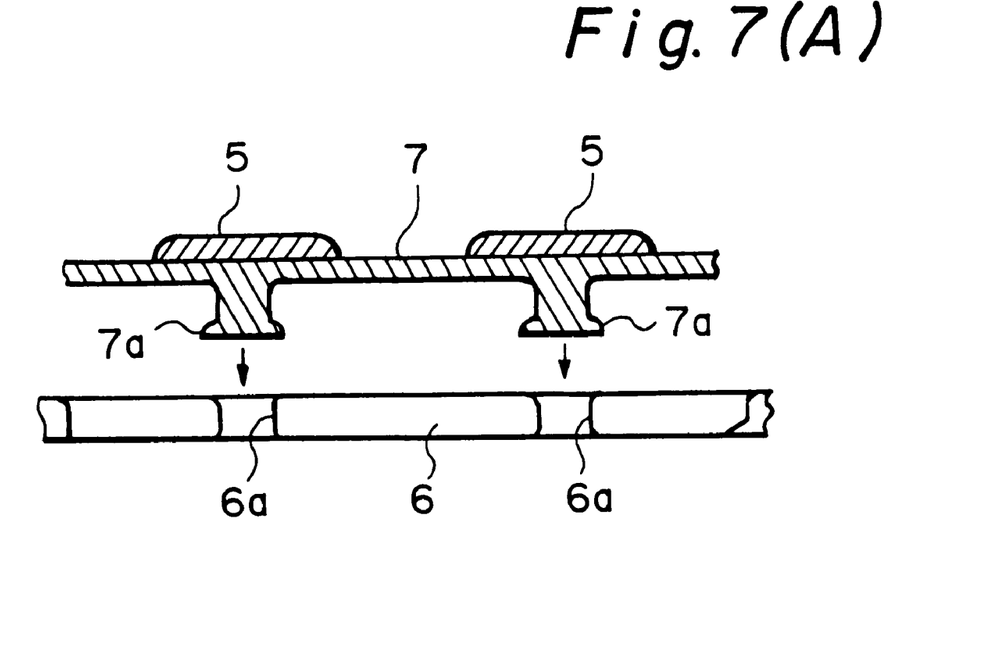
FIG. 7(A) is a sectional view of the layer structure of a band with skin adhering charge carrying pads shown in FIG. 5.
Figure 7B:
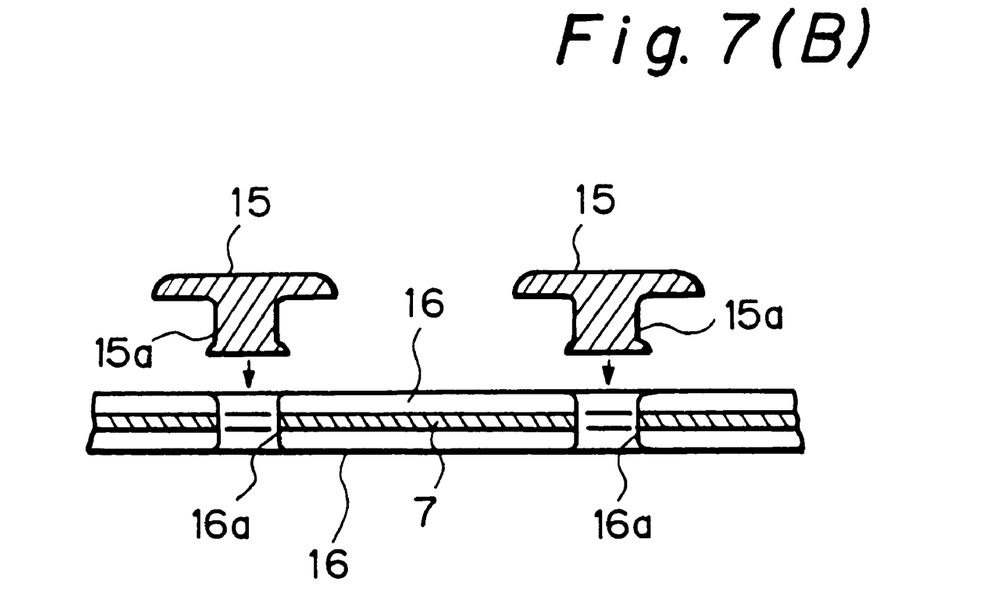
FIG. 7(B) is a sectional view of another layer structure.

The band 10 with skin adhering charge carrying pads of this example, as shown in FIG. 7(A), is structured with the engagement projections 7a of the conductive wiring 7 fit in the engagement holes 6a of the flexible attachment belt 6. Charge carrying pads 6 of unnecessary locations on the conductive wiring 7 may be removed. Further, the number of charge carrying pads 5 may be increased as well. The invention is not limited to this structure. As shown in FIG. 7(B), it may be a sandwiched layer structure comprised of a conductive wiring 7 covered by an attachment belt 16 and 16 on the two sides, wherein the engagement projections 15a of the charge carrying pads 15 are fit with the engagement holes 16a.

Note that the invention is not limited to just the above charge carrying pads. For example, it is possible to use an electrotherapy device to which magnetic pads (magnetic granules) are attached as well.

As explained above, the present invention is characterized by using a skin adhering charge carrying pad as a new electrotherapy device and using a kneading material such as a soft material or elastic material comprised of a plastic insulating substance in which a powder of charcoal is dispersed as a skin adhering charge carrying pad. The following distinctive effects were exhibited.

(1) It is possible to continuously adhere pads to suitable locations on the body according to the symptoms and possible to expect an excellent result effective against various symptoms due to the local action of the charge carrying pads. It is possible to provide a handy, user friendly electrotherapy device. Further, it is possible to realize a reduction in the treatment costs. In particular, since a kneading material such as a soft material or elastic material using a plastic insulating material as a binder is used as the skin adhering charge carrying pad, it is possible to eliminate the discomfort at the time of adhesion to the skin.

(2) If plant charcoal is used as the powder of charcoal, the sustainability of the charge becomes longer.

(3) In particular, with mugwort charcoal, the charge carrying pad has a high charge and high sustainability.

(4) If a silicone rubber plastic insulating substance is used as a binder, the viscoelasticity and kneadability can be maintained as they are. Rekneading becomes possible at any time by the fingers etc. A large amount of static electricity is generated by he friction at the time of kneading, so easy recharging of the charge carrying pads is possible and repeated use becomes possible.

(5) If more than 5 wt % of charcoal powder is intermixed, the chargeability becomes higher.

(6) By attaching the band with skin adhering charge carrying pads to the body, it is possible to apply an electrostatic field to a plurality if locations of diseased areas or pressure points and improve the ease of use. Further, if a charge is applied to the power terminals, it is possible to replenish the charge carried by the charge carrying pads through the conductive wiring and possible to achieve sustainability of the electrostatic field.

(7) By using a charging device for replenishing the charge carried by the skin adhering charge carrying pads, it is possible to achieve easy replenishing of the charges.

What is claimed is:

1. An electrotherapy device comprising a skin adhering charge carrying pad including a soft material or elastic material formed by kneading and dispersing charcoal powder with a plastic insulating substance.

2. An electrotherapy device as set forth in claim 1, characterized in that said charcoal is plant charcoal.

3. An electrotherapy device as set forth in claim 2, wherein said plant charcoal is mugwort charcoal.

4. An electrotherapy device as set forth in any one of claim 1, 2 or 3, characterized in that said plastic insulating substance is a silicone rubber.

5. An electrotherapy device as set forth in claim 4, characterized in that the ratio of mixture of the powder of charcoal in the silicone rubber is at least 5 wt %.

6. A band with skin adhering charge carrying pads comprising:
   an attachment band to which one or more of the skin adhering charge carrying pads are attached to at least one side;
   conductive wiring connected to the skin adhering charge carrying pads along said attachment band, said skin adhering charge carrying pads including a soft material or elastic material formed by kneading and dispersing charcoal powder with a plastic insulating substance; and
   power terminals provided at part of the conductive wiring.

7. A band with skin adhering charge carrying pads as set forth in claim 6, characterized in that said charcoal is plant charcoal.

8. A band with skin adhering charge carrying pads as set forth in claim 7, wherein said plant charcoal is mugwort charcoal.

9. A band with skin adhering charge carrying pads as set forth in any one of claim 6 to claim 8, characterized in that said plastic insulating substance is a silicone rubber.

10. A band with skin adhering charge carrying pads as set forth in claim 9, characterized in that the ratio of mixture of the powder of charcoal in the silicone rubber is at least 5 wt %.

11. A charging device characterized by replenishing a carried charge, by application of an electrical charge, to skin adhering charge carrying pads including a soft material or elastic material formed by kneading and dispersing charcoal powder with a plastic insulating substance.

12. A charging device as set forth in claim 11, characterized in that said charcoal is plant charcoal.

13. A charging device as set forth in claim 12, wherein said plant charcoal is mugwort charcoal.

14. A charging device as set forth in any one of claim 11 to claim 13, characterized in that said plastic insulating substance is a silicone rubber.

15. A charging device as set forth in claim 14, characterized in that the ratio of mixture of the powder of charcoal in the silicone rubber is at least 5 wt %.

16. A charging device as set forth in claim 15, wherein a band with skin adhering charge carrying pads is provided comprising:
   an attachment band to which one or more of the skin adhering charge carrying pads are attached to at least one side, said skin adhering charge carrying pads including a soft material or elastic material formed by kneading and dispersing charcoal powder with a plastic insulating substance;
   conductive wiring connected to the skin adhering charge carrying pads along said attachment band, and
   power terminals provided at part of the conductive wiring.

* * * * *